United States Patent [19]

Mickle et al.

[11] Patent Number: 5,080,886

[45] Date of Patent: Jan. 14, 1992

[54] PHARMACEUTICAL COMPOSITIONS FOR THE PREVENTION AND TREATMENT OF OXIDANT INJURIES

[75] Inventors: Donald A. G. Mickle; Tai-Wing Wu, both of Toronto, Canada

[73] Assignee: Sterling Drug Inc., New York, N.Y.

[21] Appl. No.: 461,599

[22] Filed: Jan. 5, 1990

[51] Int. Cl.$^5$ .............. A61K 31/47; A61K 31/35; A61K 37/48; A61K 37/50

[52] U.S. Cl. .................. 424/10; 424/94.4; 514/311; 514/456; 514/474

[58] Field of Search .............. 514/456, 474, 311; 424/94.4, 10

[56] References Cited

U.S. PATENT DOCUMENTS

| | | | |
|---|---|---|---|
| 4,708,964 | 11/1987 | Allen | 514/464 |
| 4,742,066 | 5/1988 | Deckner et al. | 514/456 |
| 4,847,267 | 7/1989 | Deckner et al. | 514/456 |
| 4,877,810 | 10/1989 | Mickle et al. | 514/456 |
| 4,954,332 | 9/1990 | Bissett et al. | 514/474 |
| 4,970,216 | 11/1990 | Deckner et al. | 514/456 |

FOREIGN PATENT DOCUMENTS

325826  12/1988  European Pat. Off.

OTHER PUBLICATIONS

Marx, J. L. "Oxygen Free Radicals Linked to Many Diseases" *Science* 235, 529-531 (1987).

Simpson, P. L. and B. R. Lucchesi "Free radicals and myocardial ischemia and reperfusion injury" *J. Lab. Clin. Med.*, 110, 13-30 (1987).

Jolly, S. R. et al. "Canine Myocardial Reperfusion Injury" *Circulation Research* 54, 277-285 (1984).

Ambrosio, G. et al. "Evidence for a reversible oxygen radical-mediated component of reperfusion injury: reduction by recombinant human superoxide dismutase administered at the time of reflow" *Circulation* 75, 282-291 (1987).

Ambrosio, G. et al. "Reduction in experimental infarct size by recombinant human superoxide dismutase: insights into the pathophysiology of reperfusion injury" *Circulation* 74, 1424-1433 (1986).

Aoki, N. et al. "Cardioprotective actions of human superoxide dismutase in two reperfusion models of myocardial ischaemia in the rat" *Brit. J. Pharmacol.* 95, 735-740 (1988).

Werns, S. W. et al. "The Independent Effects of Oxygen Radical Scavengers on Canine Infarct Size" *Circ. Res.* 56, 895-898 (1985).

Uraizee, A. et al. "Failure of superoxide dismutase to limit size of myocardial infarction after 40 minutes of ischemia and 4 days of reperfusion in dogs" *Circulation* 75, 1237-1248 (1987).

Nejima, J. et al. "Superoxide Dismustase Reduces Reperfusion Arrhythmias but Fails to Salvage Regional Function or Myocardium at Risk in Conscious Dogs" *Circulation* 79, 143-153 (1989).

Klein, H. H. et al. "Intracoronary SOD for the treatment of 'reperfusion injury' A blind randomized placebo-controlled trial in ischemic, reperfused porcine hearts" *Basic Res. Cardiol.* 83, 141-148 (1988).

Gee, C. A. et al. "Peroxy free radicals, enzymes and radiation damage: sensitization by oxygen and protection by superoxide dismutase and antioxidants" *Brit. J. Radiol.* 58, 251-256 (1985).

Casini, A. F. et al. "Liver Glutathione Depletion Induced by Bromobenzene, Iodobenzene, and Diethylmaleate Poisoning and Its Relation to Lipid Peroxidation and Necrosis" *Am. J. Pathol.* 118, 225-237 (1985).

Sandy, M. S. et al. "Role of Redox Cycling and Lipid Peroxidation in Bipyridyl Herbicide Cytotoxicity" *Biochem. Pharmacol.* 35, 3095-3101 (1986).

Wolf, H. R. D. and H. W. Seeger "Experimental and Clinical Results in Shock Lung Treatment with Vitamin E" *Ann. N.Y. Acad. Sci.* 393, 392-410 (1982).

Wolf et al. "Protective effect of the antioxidative chroman structure of tocopherol on the consequences of stimulated arachidonic acid release in the pulmonary vascular system" *Klin. Wochensch.* 59, 463-465 (1981) (Translation).

Kato, K. et al. "Studies on Scavengers of Active Oxygen Species. 1. Synthesis and Biological Activity of 2-0-Alkylascorbic Acids" *J. Med. Chem.* 31, 793-798 (1988).

Woodward, B. and M. N. M. Zakaria "Effect of Some Free Radical Scavengers on Reperfusion Induced Arrhythmias in the Isolated Rat Heart" *J. Molec. Cell. Cardiol.* 17, 485-493 (1985).

Takenaka, M. et al. "Protective effects of α-tocopherol and coenzyme $Q_{10}$ on warm ischemic damages of the rat kidney" *Transplantation* 32, 137-141 (1981).

Fujimoto, S. et al. "The Protective Effect of Vitamin E on Cerebral Ischemia" *Surg. Neurol.* 22, 449-454 (1984).

Marubayashi, S. et al. "Role of free radicals in ischemic rat liver cell injury: Prevention of damage by α-tocopherol administration" *Surgery* 99, 184-192 (1986).

(List continued on next page.)

*Primary Examiner*—Shep K. Rose
*Attorney, Agent, or Firm*—Philip E. Hansen; Paul E. Dupont

[57] ABSTRACT

The combination of 6-hydroxy-2,5,7,8-tetramethylchroman-2-carboxylic acid with a superoxide dismutase optionally containing a catalase and ascorbic acid provides enhanced protection from oxidant injury.

Administration of 6-hydroxy-2,5,7,8-tetramethyl chroman-2-carboxylic acid, SOD, and optionally CAT and/or ascorbic acid prior to or simultaneously with resuming normal blood supply to mammalian tissue following ischemia provides substantial protection from tissue damage that otherwise is observed upon reperfusion. Administration of Vitamin E, SOD, and CAT similarly provide protection from oxidant injury.

18 Claims, No Drawings

OTHER PUBLICATIONS

Cavarocchi, N. C. et al. "Superoxide Generation During Cardiopulmonary Bypass: Is There a Role for Vitamin E?" *J. Surg. Res.* 40, 519–527 (1986).

Sarret, M. et al. "Ischemia and reperfusion-induced arrhythmias in the anesthetized rat, Effect of ubiquinone alpha tocopherol and superoxide dismutase" *Cardiologia* 31, 539–544 (1986); *Biol. Abst.* Acc. No. 84063823 (1987).

Ferrari, R. et al. "Role of oxygen in myocardial ischaemic and reperfusion damage, Effect of alpha-tocopherol" *Acta Vitaminol. Enzymol.* 7 *Suppl.* 61–70 (1985); *Medline Abst.* No. 87045647.

Massey, K. D. and K. P. Burton "α-Tocopherol attenuates myocardial membrane-related alterations resulting from ischemia and reperfusion" *Am. J. Physiol.* 256, H1192–1199 (1989).

Klein, H. H. et al. "Combined treatment with Vitamins E and C in experimental myocardial infarction in pigs" *Am. Heart. J.* 118, 667–673 (1989).

Mickle, D. A. G. et al. "Myocardial salvage with Trolox and ascorbic acid for an acute evolving infarction" *Ann. Thorac. Surg.* 47, 553–557 (1989).

PHARMACEUTICAL COMPOSITIONS FOR THE PREVENTION AND TREATMENT OF OXIDANT INJURIES

BACKGROUND OF THE INVENTION

1. Field of the Invention

The invention relates to compositions for the prevention and treatment of oxidant injury, particularly reperfusion injury, and to the method of use of such compositions and their components in mammals. Reperfusion injury has been observed to occur upon reperfusion following ischemia caused, for example, by blood clots, organic repair or transplant surgery.

2. Information Disclosure

A number of causes and mechanisms have been suggested for the damage that occurs to tissue after ischemia and reperfusion. While it is likely that a variety of causes and mechanisms contribute to the damage, a popular current theory that is supported by experimental evidence involves the generation of free radicals upon reperfusion. See J. L. Marx, "Oxygen Free Radicals Linked to Many Diseases," *Science,* Research News, 30 January 1987, pp. 529–531. The current consensus on the role of free radicals in reperfusion injury in the heart is discussed in a recent review article entitled "Free Radicals and Myocardial Ischemia and Reperfusion Injury," (Simpson and Lucchesi J. W. *Lab. Med.,* July, 1987) which lists 146 references.

There are a number of reports in the literature of the use of superoxide dismutase (SOD) with or without catalase (CAT) for the prevention and treatment of reperfusion injury: Jolly et al. [*Circulation Research* 54, 277–285 (1984)] describe the beneficial effects of SOD plus CAT on infarct size in dogs. The SOD/CAT infusion is begun 15 minutes before a 90-minute occlusion and continues 15 minutes into reperfusion. Ambrosio et al. [*Circulation* 74, 1424–1433(1986)] describe the significant decrease in infarct size in the hearts of dogs treated with SOD at reperfusion after 90 minutes of proximal circumflex coronary artery occlusion. Similarly Ambrosio et al. [*Circulation* 75, 282–291(1987)] describe the significant improvement in isovolumic left ventricular developed pressure and phosphocreatine levels in Langendorff perfused rabbit hearts following 30 minutes of normothermic global ischemia when SOD was administered at reperfusion. The addition of CAT showed no benefit above that seen with SOD. Aoki et al. [*Brit. J. Pharmacol.* 95, 735–740(1988)] describe the significant attenuation of elevated post-perfusion pressure and protection against loss of myocardial creatine kinase activity in rats and perfused rat hearts upon administration of SOD after occlusion and after reperfusion. Werns et al. [*Circulation Research* 56, 895–898 (1985)] describe the beneficial effects of SOD but not CAT on infarct size in dogs after a 90-minute occlusion. European application 295826 discloses the use of SOD in open heart surgery to prevent reperfusion injury.

There have also been reports in the literature of the failure of SOD, with and without CAT, to effect any useful salvage of ischemic tissue: Uraizee et al. [*Circulation* 75, 1237–1248(1987)] reported that SOD before and during initial reperfusion after 40 minutes of circumflex coronary artery occlusion did not limit infarct size in dogs. Nejima et al. [*Circulation* 79, 143–153(1989)] reported that SOD and catalase did not improve regional myocardial dysfunction or infarct size in conscious dogs after 90-minute coronary artery occlusion. Klein et al. [*Basic Res Cardiol.* 83, 141–148 (1988)] disclose that recombinant human SOD administered two minutes before and for 45 minutes after initiation of reperfusion did not significantly reduce infarct size or diminish arrhythmia in pigs after 45-minute occlusion.

6-Hydroxy-2,5,7,8-tetramethylchroman-2-carboxylic acid, also known as Trolox® C, has been reported to protect alcohol dehydrogenase from radiation damage [Gee et al. *Brit. J. Radiol.* 58, 251–256 (1985)] and to protect rat liver from the peroxidative damage caused by halobenzene poisoning [Casini et al. Am. J. Pathol. 118, 225–237 (1985)], although it did not protect isolated hepatocytes from herbicide poisoning [Sandy et al. *Biochem. Pharmacol.* 35, 3095–3101 (1986)]. Trolox® C was also reported to protect isolated perfused rabbit lungs from the pulmonary arterial pressure reaction provoked by the perfusion with a calcium ionophore; the effect was attributed to inhibition of cyclooxygenase and lipoxygenase activity by antioxidants [Wolf et al. *Ann. N. Y. Acad. Sci.* 393, 392–410 (1982) and *Klinische Wochenschrift* 59, 463–465 (1981)].

Kato et al. [*J. Med. Chem.* 31, 793–798 (1988)] reported that several acylated 2,3-enediol congeners of ascorbic acid were effective, when given prophylactically, in inhibiting reperfusion injury in the rat LAD model of myocardial ischemia. They further reported that both Vitamin E and ascorbic acid were without effect in this model. Woodward and Zakaria [*J. Molec. Cell. Cardiol.* 17, 485–493 (1985)] reported that ascorbic acid introduced after restriction and before reperfusion, reduced the incidence and duration of ventricular fibrillation in an isolated perfused rat heart model of reperfusion-induced arrhythmia.

The prophylactic use of Vitamin E to reduce the amount of tissue damage upon reperfusion of ischemic tissue in the kidney [Takenaka et al. *Transplantation* 32, 137–141 (1981)], in the brain [Fujimoto et al. *Surg. Neurol.* 22, 449–454 (1984)], and in the liver [Marubayashi et al. op. cit.] has been described. In the heart, the prophylactic use of Vitamin E has been reported to be successful in some paradigms [Cavarocchi et al. *J. Surg. Research* 40, 519–527 (1986) and Sarrett et al. *Cardiologia* 31, 539–544 (1986); *Biol. Abs.* 84063823 (1987)] but not in others [Ferrari et al. *Acta Vitaminol Enzymol* 7 Suppl., 61–70 (1985)]. Massey and Burton [*Am. J. Physiol.* 256, H1192–H1199 (1989)] reported significant protection from reperfusion injury in isolated, perfused rat hearts when the rats had been treated with 5 mg/day of Vitamin E by continuous release for 14 days before the induction of ischemia. Klein et al [*Am. Heart J.* 118, 667–673 (1989)] administered 12 g of Vitamin E acetate by i.v. infusion during a period of six days before occlusion of the left anterior descending coronary artery of pigs. In a separate group of pigs they administered 12 g of Vitamin E acetate by intraarterial infusion after occlusion and before reperfusion. In both groups ascorbic acid (0.1 g/kg) was infused i.v. after occlusion and before reperfusion. They reported that prophylactic treatment (the first group) was highly effective in preventing reperfusion injury; acute treatment was effective but only achieved "borderline significance".

We have shown [Mickle et al. *Ann. Thorac. Surg.* 47 553–557 (1989) and U.S. Pat. No. 4,877,810] that Trolox®, and Trolox® with ascorbic acid are effective agents for the prevention and treatment of reperfusion injury. We have now discovered that SOD, catalase, Trolox®, and ascorbic acid are selectively effective in different cell types to prevent and treat oxidative injury of the type that results from ischemia and reperfusion. Thus, as shown below, ventricular fibroblasts are more resistant to free-radical injury than are ventricular myocytes, which are, in turn, more resistant than arterial endothelial cells. Myocardial fibroblasts and arterial endothelial cells are best protected by SOD and catalase, whereas myocytes are best protected by Trolox ® and ascorbic acid. This finding may help to explain the discrepant results reported for the utility of SOD/CAT and of Vitamin E in slightly differing models with differing treatment protocols and differing ways of assessing injury, all of which are based on whole-organ preparations. The results of whole-organ experiments usually reflect the mean contributions of all cell types in the organ affected. Differential effects on individual cell types resulting from ischemia-reperfusion injury, differential salvage by the treatment and differential detection by the assessment procedure are submerged in the aggregate result.

SUMMARY OF THE INVENTION

The invention relates to a method comprising the combined use of several antioxidants to produce enhanced protection and salvage of ischemic organs and tissues from the injury that is associated with reperfusion following ischemia. Thus SOD and catalase are administered substantially concurrently with Trolox ® with and without ascorbic acid for the treatment and prevention of reperfusion injury in mammals, particularly humans. Similarly, SOD and catalase are administered with Vitamin E for the treatment and prevention of reperfusion injury in mammals.

The invention also relates to pharmaceutical compositions for the treatment or prevention of oxidative injury, particularly reperfusion damage, more particularly cardiac reperfusion damage. One composition comprises SOD and Trolox ® and, preferably, additionally comprises catalase. Ascorbic acid is optionally present. A second composition comprises Vitamin E, SOD and catalase.

The invention further relates to a method for the treatment or prevention of reperfusion injury that comprises administering to a mammal pharmaceutical compositions as described above.

DETAILED DESCRIPTION INCLUSIVE OF PREFERRED EMBODIMENTS

We have found that different cell types have different susceptibilities to a free-radical injury that the art suggests is representative of the oxidative injury that accompanies the reperfusion of ischemic tissue. We have further found that different populations of cells respond differently to putative antioxidants, and thus a combination of antioxidants is more effective than each antioxidant acting alone in salvaging tissues and organs that are composed of multiple cell populations. Moreover, we have found that a combination of antioxidants acts synergistically to produce an enhanced effect even in a single cell population. Thus reperfusion injury in a mammal can be mitigated by the administration of a combination of anti-oxidants acting synergistically on individual cell types as well as acting with selective advantages in mixed cell populations.

Ventricular myocytes were prepared by washing with phosphate buffer 5 to 10 mg myocardial biopsies of the left ventricles of patients having aortocoronary bypass surgery. After dissecting out the connective tissue, the tissue was dissociated with 2% trypsin. and 0.1% collagenase. The supernatant was collected and centrifuged for 5 min at 600 g to precipitate the cells. The supernatant was discarded and the cells resuspended in culture medium containing 10% fetal bovine serum and DMEM (Dulbecco's Modified Eagle Medium, Gibco Labs, Life Technologies Inc., Grand Island, N.Y. 14072). Fibroblasts and myocytes were separated manually. Myocardial fibroblasts were cultured in DMEM medium after being separated from the myocytes. After 4 to 5 hours in the primary culture, the fibroblasts tended to attach to the Petri dish while the myocytes remained free floating and could be readily removed for culture. The ventricular myocytes were cultured in an incubator at 37° C. at a $pO_2$ of 160 mm Hg for 21 days. The identity of the myocytes was confirmed by morphological appearance, electron microscopy, and by fluorescence with antibodies to actin, to human ventricular light chain 1, and heavy chain. The fibroblasts were identified by morphological appearance.

Vascular endothelial cells were obtained from an aortic button removed from patients having aortocoronary bypass surgery. The aortic button was coated with 0.1% collagenase, and after 30 min of incubation at room temperature the cells were washed out and cultured in a medium described by Morgan, Morton and Parker [*Proc. Soc. Exp. Biol. Med.* 73, (1950)]. The medium is commercially available as 199 medium from Gibco Laboratories (U.S.A.). To identify endothelial cells other than by morphological appearance, the cells were washed with phosphate-buffered saline three times. Antibodies to factor VIII were incubated with the cells for 30 min at 37° C. The cells were then washed with phosphate-buffered saline before the addition of an anti-factor VIII conjugated with fluorescein isothiocyanate. After washing the cells with phosphate-buffered saline, the endothelial cells fluoresced under ultraviolet light. The endothelial cells were cultured at an oxygen tension of 160 mm Hg at 37°.

The cells used in the experimental studies were from passages P2 to P4. The mean number of myocytes ± 1 SD tested in each culture dish was $2.25 \pm 0.06 \times 10^5$ and did not significantly differ for any of the experimental studies. Likewise, the numbers of endothelial cells and fibroblasts in each culture dish were $4.20 \pm 0.04 \times 10^5$ and $3.60 \pm 0.12 \times 10^5$, respectively, and the counts did not differ statistically for any of the experimental studies.

The morphological criteria for cell necrosis were cell membrane rupture and cell shrinkage. The time to necrose 100,000 cells was the basis of comparison of cell sensitivities to free radical injury and the relative effectiveness of the anti-oxidants.

Free radical studies were performed by removing the cell culture medium and by adding 6.0 ml of phosphate buffered saline ( pH 7.4, 37° C.) containing xanthine oxidase (33.3 IU/L) and hypoxanthine (1 mM). The addition of hypoxanthine (N=10) alone or xanthine oxidase (N=10) alone did not produce any morphological changes by 30 min. All antioxidants tested were administered immediately prior to the addition of the free radical generation system. The concentration of Trolox ® studied was 1.34 mM or 1.0 mM. Ascorbic acid was also tested at these concentrations. SOD was tested at $2.4 \times 10^4$, $1 \times 10^6$ and $1 \times 10^7$ IU/L and catalase at $9.2 \times 10^4$, $1 \times 10^6$ and $1 \times 10^7$ IU/L. Controls with Trolox ®, ascorbic acid, SOD or catalase in phosphate buffered saline (pH 7.4, 37° C.) were run and no morphological changes were apparent at 30 mins.

The first morphological change observed in necrosing cells was a halo-like appearance around the cells followed shortly by cell membrane blebbing and then cell shrinkage. In separate experiments, the mean times $\pm 1$ SD in minutes of $1.04 \pm 0.18$, $1.90 \pm 0.6$, and $2.66 \pm 0.46$, respectively, to necrose 100,000 endothelial cells (N=5), myocytes (N=10) and fibroblasts (N=5) were significantly (p<0.01) different from each other. When myocytes with some fibroblast contamination were studied, all the myocytes were invariably necrosed by 8 to 10 min while the fibroblasts remained morphologically unchanged for longer than 30 minutes.

Table 1 shows the time in minutes $\pm$ one standard deviation to necrose $10^5$ cells. Trolox ® and ascorbic acid were more effective antioxidants than SOD and catalase in protecting the myocytes from free radical injury. The reverse was true for fibroblasts with SOD and CAT being more protective than either Trolox ® or ascorbic acid. In endothelial cells SOD and catalase were quite effective, ascorbic acid was less effective but still showed statistically significant protection, and Trolox ® was ineffective.

TABLE 1

|  | AORTIC ENDOTHELIAL CELLS | VENTRICULAR MYOCYTES | FIBROBLASTS |
|---|---|---|---|
| FREE RADICAL INJURY | 1.04 ± 0.18 | 1.90 ± 0.6 | 2.66 ± 0.46 |
| ASCORBIC ACID (1.34 mmol/L) | 1.56 ± 0.09** | 6.10 ± 1.8** | 2.88 ± 0.34 |
| TROLOX ® (1.34 MMOL/L) | 1.17 ± 0.15 | 7.10 ± 1.7** | 3.46 ± 0.48 |
| SOD (24,200 IU/L) PLUS CATALASE (92,000 IU/L) | 5.76 ± 0.52** | 2.60 ± 0.3 | 6.18 ± 0.58** |

**indicates statistical significance at the P < 0.01 level.

In a second set of experiments, myocytes were treated as before except that 50 IU/L of xanthine oxidase was used. The somewhat larger burst of radicals produced a shorter average time to necrose $10^5$ unprotected cells. Neither SOD alone nor CAT alone produced a significant increase in cell survival, as shown in Table 2:

TABLE 2

|  | Time to necrose $10^5$ myocytes |
|---|---|
| Control | 1.56 ± 0.11 |
| SOD ($10^6$ IU/L) | 1.56 ± 0.13 |
| SOD ($10^7$ IU/L) | 1.45 ± 0.22 |
| CAT ($10^6$ IU/L) | 1.41 ± 0.34 |
| CAT ($10^7$ IU/L) | 1.64 ± 0.08 |

A third set of experiments under the same conditions as the second compared Trolox ®, SOD plus CAT, Trolox ® plus SOD, Trolox ® plus CAT, and Trolox ® plus SOD plus CAT. The results are shown in Table 3:

TABLE 3

|  | Time to necrose $10^5$ myocytes |
|---|---|
| Control | 1.68 ± 0.06 |
| Trolox ® (1 mM) | 3.36 ± 0.18** |
| SOD ($10^7$ IU/L) + CAT ($10^7$ IU/L) | 1.79 ± 0.16 |
| Trolox ® (1 mM) + SOD ($10^7$ IU/L) | 3.90 ± 0.21** |
| Trolox ® (1 mM) + CAT ($10^7$ IU/L) | 2.93 ± 0.27** |
| Trolox ® (1 mM) + CAT ($10^7$ IU/L) + SOD ($10^7$ IU/L) | 8.07 ± 0.33** |

The results shown in Tables 2 and 3 support the conclusion that (1) Trolox ® is effective in protecting myocytes from free radical injury; (2) SOD and CAT, alone or together are ineffective in protecting myocytes; (3) Trolox ® plus SOD is more effective than Trolox ® alone; (4) Trolox ® plus CAT is no more effective than Trolox ® alone; and (5) although SOD and CAT are totally without effect in myocytes, the combination of Trolox ®, SOD and CAT is almost twice as effective as Trolox ® alone.

Thus a combination of Trolox ® and SOD, optimally including catalase, and optionally including ascorbic acid, will provide superior protection from reperfusion injury to that provided by any of the components alone.

A fourth set of experiments under the same conditions as the second and third compared d,l-α-tocopheryl acetate [Aquasol-E ™, USV Canada] (α-T) alone, α-T plus SOD, α-T plus CAT, SOD plus CAT, and α-T plus SOD plus CAT. The results are shown in Table 4:

TABLE 4

|  | Time to necrose $10^5$ myocytes |
|---|---|
| Control | 1.65 ± 0.09 |
| d,1-α-tocopheryl acetate (1 mM = 470 IU/L) | 3.41 ± 0.30 |
| α-T (1 mM) + SOD ($10^7$ IU/L) | 3.66 ± 0.18 |
| α-T (1 mM) + CAT ($10^7$ IU/L) | 3.40 ± 0.11 |
| SOD ($10^7$ IU/L) + CAT ($10^7$ IU/L) | 1.64 ± 0.08 |
| α-T (1 mM) + SOD + CAT ($10^6$ IU/L) | 6.26 ± 0.57 |
| α-T (1 mM) + SOD + CAT ($10^7$ IU/L) | 6.76 ± 0.51 |

The results shown in Table 4 support the conclusions that (1) Vitamin E is effective in protecting myocytes from free radical injury; (2) SOD and CAT together are ineffective; (3) SOD with Vitamin E and CAT with Vitamin E are no more effective than Vitamin E alone; but the combination of Vitamin E, SOD and CAT is almost twice as effective as Vitamin E alone. Thus a combination of Vitamin E, SOD and catalase will provide superior protection from reperfusion injury to that provided by any of the components alone.

A superoxide dismutase is an enzyme that catalyzes the breakdown of the superoxide anion radical ($O_2 \approx$) to oxygen and hydrogen peroxide. A substance having superoxide dismutase activity is thus any substance that catalyzes the conversion of superoxide to hydrogen peroxide and oxygen. For example, naturally occurring proteinaceous enzymes, their functionally competent analogs and muteins, and such low molecular weight SODs as are described in U.S. Pat. Nos. 4,655,054 and 4,760,051 constitute superoxide dismutases for the purposes of this invention.

In formulations of the invention SOD may be of any origin. SOD is known under the systematic nomenclature of the International Union of Biochemistry as superoxide oxidoreductase and has a classification number of 1.15.1.1. Both copper-zinc and manganese-iron SODs are contemplated within the invention.

SOD is commercially obtained from bovine erythrocytes, human erythrocytes, *Bacillus stearothermophilus, E. coli* and horseradish. Mammalian SOD is also obtained by recombinant synthesis in microorganisms such as *E. coli* and yeast. Human and bovine SOD are preferred.

For the purposes of the invention SOD may also be complexed or covalently linked to polymers to provide conjugates that retain enzymic activity. Such conjugates may possess improved pharmacodynamic and metabolic characteristics. Some typical SOD conjugates are disclosed, for example, in European applications 210761 and 200467, Japanese applications 58/032826 and 59/175885, PCT application 89/01033, and U.S. Pat. No. 4,563,349. Preferred conjugates comprise recombinant or native human SOD or bovine SOD covalently linked to polyethylene glycol (PEG) as described in U.S. Pat. No. 4,179,337. A PEG-SOD conjugate is commercially available from Sigma (USA). In a preferred embodiment the PEG has a molecular weight from $1 \times 10^3$ to $2 \times 10^5$, preferably $1 \times 10^3$ to $2 \times 10^4$, and the conjugate is from about 40 to about 99 weight percent, preferably about 45 to about 60 weight percent, PEG. It is preferred that the SOD or SOD conjugate have an activity greater than about 1,000 IU/mg as determined by the method of Fridovich and McCord [*J. Biol. Chem.* 244, 6049-6055(1969)].

A catalase is an enzyme that catalyzes the conversion of hydrogen peroxide to water and oxygen. A substance having catalase activity for the purpose of this invention is thus any substance that catalyzes the conversion of hydrogen peroxide to water and oxygen.

In formulations of the invention CAT may also be of any origin. CAT is known under the systematic nomenclature of the International Union of Biochemistry as hydrogen peroxide: hydrogen peroxide oxidoreductase and has a classification number of 1.11.1.6. CAT is commercially obtained from mammalian liver—primarily bovine liver—and from microorganisms such as *Aspergillus niger*. As in the case of SOD, CAT may be covalently linked with polymers to provide conjugates that retain enzymic activity. One such conjugate that is commercially available (Sigma, U.S.A.) comprises CAT linked to polyethylene glycol according to the method of Abuchowski et al. [*J. Biol. Chem.* 252, 3582-3586 (1977)] It is preferred that the CAT or conjugated CAT have an activity of greater than 1,000 IU/mg as measured by the peroxide reduction method of Beers and Fizer [*J. Biol. Chem.* 195, 133-140(1952)]. The instant invention contemplates the use of either the free CAT enzyme or a conjugate of CAT that retains CAT activity.

The term "Vitamin E" refers to the nomenclature proposed by the American Institute of Nutrition and is consistent with the nomenclature proposed by the International Union of Pure and Applied Chemists: "The term Vitamin E should be used as the generic description for all tocol and tocotrienol derivatives qualitatively exhibiting the biological activity of α-tocopherol." Examples of substances that would be encompassed by the term Vitamin E would include d,l-α-tocopheryl acetate; d,l-α-tocopherol; d,α-tocopheryl acetate; d,α-tocopherol; d,l-α-tocopheryl acid succinate; and d,α-tocopheryl acid succinate. Further examples and a description of the nomenclature may be found in *Handbook of Vitamins*, Lawrence J. Machlin ed., Marcel Dekker, N.Y. 1984, pages 101-105, which is incorporated herein by reference.

A composition of the invention comprises from about 0.2 g/L to about 10 g/L, preferably from about 3 g/L to about 6 g/L, of 6-hydroxy-2,5,7,8-tetramethyl-chroman-2-carboxylic acid, from about $1 \times 10^3$ to about $1 \times 10^8$ IU/L, preferably from about $1 \times 10^6$ to $1 \times 10^7$ IU/L, of SOD, from zero to about $1 \times 10^8$ IU/L, preferably about $1 \times 10^3$ to about $1 \times 10^8$ IU/L, more preferably from about $1 \times 10^6$ to $1 \times 10^7$ IU/L, of catalase, and from about zero to about 10 g/L of ascorbic acid. If ascorbic acid is present, it is preferably at a concentration between about 2 g/L and about 6 g/L. The composition may be administered in any pharmaceutically acceptable vehicle. An aqueous vehicle is preferred for direct administration into a blood vessel. Typical vehicles are physiological saline, aqueous dextrose, Ringer's lactate and similar intravenous and cardioplegic solutions known in the art.

A second composition of the invention comprises from about 150 IU/L to about 1,500 IU/L of Vitamin E, from about $1 \times 10^3$ to about $1 \times 10^8$ IU/L, preferably about $1 \times 10^6$ to about $1 \times 10^7$ IU/L of SOD, and from about $1 \times 10^3$ to about $1 \times 10^8$ IU/L, preferably about $1 \times 10^6$ to about $1 \times 10^7$ IU/L, of catalase. The composition may be administered in any pharmaceutically acceptable vehicle. An aqueous vehicle is preferred for direct administration into a blood vessel. Typical vehicles are physiological saline, aqueous dextrose, Ringer's lactate and similar intravenous and cardioplegic solutions known in the art.

While introduction of the compositions of the invention directly into the bloodstream is the presently preferred route of administration, the invention also contemplates intramuscular as well as intraperitoneal administration under appropriate circumstances. Other suitable forms of administration within the scope of the present invention include oral and cardioplegic, either alone or in combination with other forms of administration, such as those described above, particularly for such conditions as scheduled surgery involving heart by-pass or organ or tissue transplant.

The timing of administration is not critical as long as the components ar present in the target tissue in effective concentrations at the time that the burst of free radicals occurs. Thus administration may be begun at any time before reperfusion or substantially concurrently with reperfusion; administration substantially after reperfusion has begun will result in diminished protection that decreases to no protection as a function of the time between initiation of reperfusion and initiation of therapy.

We claim:

1. A solution composition for the treatment or prevention of cardiac reperfusion damage in mammals comprising from about 0.2 g/L to about 10 g/L of 6-hydroxy 2,5,7,8-tetramethylchroman-2-carboxylic acid, and from about $1 \times 10^3$ IU/L to about $1 \times 10^8$ IU/L of a dismutating substance chosen from the group consisting of superoxide dismutases and SOD conjugates in a pharmaceutically acceptable aqueous vehicle.

2. A composition according to claim 1 further comprising from about $1 \times 10^3$ to about $1 \times 10^8$ IU/L of a catalyzing substance chosen from the group consisting of catalases and catalase conjugates.

3. A composition according to claim 2 further comprising from about 0.2 g/L to about 10 g/L of ascorbic acid.

4. A composition according to claim 1 wherein said dismutating substance is a superoxide dismutase conjugate.

5. A composition according to claim 2 wherein said catalyzing substance is a catalase conjugate.

6. A composition according to claim 1 wherein said dismutating substance is a superoxide dismutase.

7. A composition according to claim 2 wherein said dismutating substance is a superoxide dismutase and said catalyzing substance is a catalase.

8. A composition according to claim 7 comprising from about 3 g/L to about 6 g/L of 6-hydroxy-2,5,7,8-tetramethylchroman -2-carboxylic acid, from about $1 \times 10^6$ to about $1 \times 10^7$ IU/L of superoxide dismutase, and from about $1 \times 10^6$ IU/L to about $1 \times 10^7$ IU/L of catalase.

9. A composition according to claim 8 further comprising from about 2 g/L to about 6 g/L of ascorbic acid.

10. A pharmaceutical composition comprising from about 150 IU/L to about 1,500 IU/L of Vitamin E, from about $1 \times 10^3$ to about $1 \times 10^8$ IU/L of a dismutating substance chosen from the group consisting of superoxide dismutases and SOD conjugates and from about $1 \times 10^3$ to about $1 \times 10^8$ IU/L of a catalyzing substance chosen from the group consisting of catalases and catalase conjugates.

11. A method for the treatment or prevention of reperfusion injury in mammals which comprises administering to a mammal in need of such treatment effective amounts of 6-hydroxy-2,5,7,8-tetramethylchroman-2-carboxylic acid and a dismutating substance chosen from the group consisting of superoxide dismutases and SOD conjugates.

12. A method for the treatment or prevention of reperfusion injury according to claim 11 which comprises administering to a mammal in need of such treatment from about 0.2 g/L to about 10 g/L of 6-hydroxy-2,5,7,8-tetramethylchroman -2-carboxylic acid and from about $1 \times 10^3$ IU/L to about $1 \times 10^8$ IU/L of a dismutating substance chosen from the group consisting of superoxide dismutases and SOD conjugates.

13. A method for the treatment or prevention of reperfusion injury in mammals which comprises administering to a mammal in need to such treatment from about 0.2 g/L to about 10 g/L of 6-hydroxy-2,5,7,8-tetramethylchroman-2-carboxylic acid, from about $1 \times 10^3$ to about $1 \times 10^8$ IU/L of a dismutating substance chosen from the group consisting of superoxide dismutases and SOD conjugates, and from about $1 \times 10^3$ to about $1 \times 10^8$ IU/L of a catalyzing substance chosen from the group consisting of catalases and catalase conjugates.

14. A method according to claim 13 wherein said dismutating substance is a superoxide dismutase and said catalyzing substance is a catalase.

15. A method for the treatment or prevention of cardiac reperfusion injury in mammals which comprises administering to a mammal in need of such treatment a composition according to claim 1.

16. A method for the treatment or prevention of cardiac reperfusion injury in mammals which comprises administering to a mammal in need of such treatment a composition according to claim 9.

17. A method for the treatment or prevention of reperfusion injury in mammals which comprises administering to a mammal in need of such treatment effective amounts of Vitamin E, a dismutating substance chosen from the group consisting of superoxide dismutases and SOD conjugates, and a catalyzing substance chosen from the group consisting of catalases and catalase conjugates.

18. A method for the treatment or prevention of reperfusion injury in mammals which comprises administering to a mammal in need of such treatment a composition according to claim 10.

* * * * *